12) United States Patent
Schuh et al.

(10) Patent No.: US 10,900,081 B2
(45) Date of Patent: Jan. 26, 2021

US010900081B2

(54) NON-INVASIVE PRENATAL SCREENING

(71) Applicant: OXFORD UNIVERSITY INNOVATION LIMITED, Oxford (GB)

(72) Inventors: Anna Schuh, Oxford (GB); Shirley Jane Henderson, Oxford (GB)

(73) Assignee: Oxford University Innovation Limited, Oxford (GB)

( * ) Notice: Subject to any disclaimer, the term of this patent is extended or adjusted under 35 U.S.C. 154(b) by 264 days.

(21) Appl. No.: 14/774,865

(22) PCT Filed: Mar. 14, 2014

(86) PCT No.: PCT/GB2014/050810
§ 371 (c)(1),
(2) Date: Sep. 11, 2015

(87) PCT Pub. No.: WO2014/140630
PCT Pub. Date: Sep. 18, 2014

(65) Prior Publication Data
US 2016/0053320 A1 Feb. 25, 2016

(30) Foreign Application Priority Data
Mar. 15, 2013 (GB) .................................. 1304810.3

(51) Int. Cl.
C12Q 1/6883 (2018.01)
C12Q 1/6858 (2018.01)

(52) U.S. Cl.
CPC ......... C12Q 1/6883 (2013.01); C12Q 1/6858 (2013.01); C12Q 2600/156 (2013.01); C12Q 2600/16 (2013.01); C12Q 2600/172 (2013.01)

(58) Field of Classification Search
None
See application file for complete search history.

(56) References Cited

U.S. PATENT DOCUMENTS

| 6,258,540 B1 | 7/2001 | Lo et al. | |
|---|---|---|---|
| 6,582,908 B2 * | 6/2003 | Fodor ................... | B01J 19/0046 435/288.3 |
| 2004/0137470 A1 | 7/2004 | Dhallan | |
| 2006/0183136 A1 | 8/2006 | Pont-Kingdon et al. | |
| 2010/0298152 A1 * | 11/2010 | Brown .................... | C12N 15/111 506/4 |
| 2011/0244455 A1 * | 10/2011 | Larson .................. | C12Q 1/6816 435/6.11 |
| 2012/0164646 A1 | 6/2012 | Song et al. | |
| 2012/0196754 A1 * | 8/2012 | Quake ................... | C12Q 1/6806 506/2 |
| 2012/0264121 A1 * | 10/2012 | Rava ....................... | G16B 30/00 435/6.11 |
| 2013/0230858 A1 * | 9/2013 | Cantor ................. | C12Q 1/6804 435/6.12 |

FOREIGN PATENT DOCUMENTS

| EP | 2559774 | 2/2013 |
|---|---|---|
| WO | WO 2007/147018 | 12/2007 |
| WO | WO 2011/091046 | 7/2011 |
| WO | WO 2012/058316 | 5/2012 |
| WO | WO 2012/103031 | 8/2012 |

OTHER PUBLICATIONS

Barrett et al. "Digital PCR Analysis of Maternal Plasma for Non-invasive Detection of Sickle Cell Anemia," Clinical Chemistry, Jun. 2012, vol. 58, No. 6, pp. 1026-1032.
Lam et al. "Noninvasive Prenatal Diagnosis of Monogenic Diseases by Targeted Massively Parallel Sequencing of Maternal Plasma: Application to β-Thalassemia," Clinical Chemistry, Oct. 2012, vol. 58, No. 10, pp. 1467-1475.
Liao et al. "Targeted Massively Parallel Sequencing of Maternal Plasma DNA Permits Efficient and Unbiased Detection of Fetal Alleles," Clinical Chemistry, Jan. 2011, vol. 57, No. 1, pp. 92-101.
Papasavva et al. "A Minimal Set of SNPs for the Noninvasive Prenatal Diagnosis of β-Thalassaemia," Annals of Human Genetics, Mar. 2013, vol. 77, No. 2, pp. 115-124.
Tong et al. "Noninvasive Prenatal Detection of Fetal Trisomy 18 by Epigenetic Allelic Ratio Analysis in Maternal Plasma: Theoretical and Empirical Considerations," Clinical Chemistry, Oct. 2006, vol. 52, No. 12, pp. 2914-2202.
White et al. "Evaluation of a Novel Assay for Detection of the Fetal Marker RASSF1A: Facilitating Improved Diagnostic Reliability of Noninvasive Prenatal Diagnosis," PLOS one, Sep. 2012, vol. 7, No. 9, e45073, 5 pages.
Yan et al. "Reliable Detection of Paternal SNPs within Deletion Breakpoints for Non-Invasive Prenatal Exclusion of Homozygous α-Thalassemia in Maternal Plasma." PloS one, Sep. 2011, vol. 6, No. 9, e24779, 9 pages.
Zimmerman et al. "Noninvasive prenatal aneuploidy testing of chromosomes 13, 18, 21, X, and Y, using targeted sequencing of polymorphic loci," Prenatal Diagnosis, Oct. 2012, vol. 32, No. 13, pp. 1233-1241.
Search Report for United Kingdom Patent Application No. GB1304810. 3, dated Sep. 27, 2013, 4 pages.
International Search Report and Written Opinion for International (PCT) Patent Application No. PCT/GB2014/050810, dated Jun. 3, 2014, 15 pages.

* cited by examiner

Primary Examiner — Katherine D Salmon
(74) Attorney, Agent, or Firm — Sheridan Ross P.C.

(57) ABSTRACT

The present invention is concerned with prenatal screening and in particular non-invasive prenatal screening, as well as primers, primer sets and kits. In one instance, the invention provides a method of prenatal screening comprising: (a) amplifying a region encompassing the site of a mutation site responsible for the disorder, the amplification being performed on a DNA sample obtained from a pregnant female which comprises both maternal and fetal DNA; (b) sequencing a plurality of products from the amplification and determining whether or not the mutant allele is represented at a different frequency to that expected from the genotype of the pregnant female alone.

18 Claims, 10 Drawing Sheets
Specification includes a Sequence Listing.

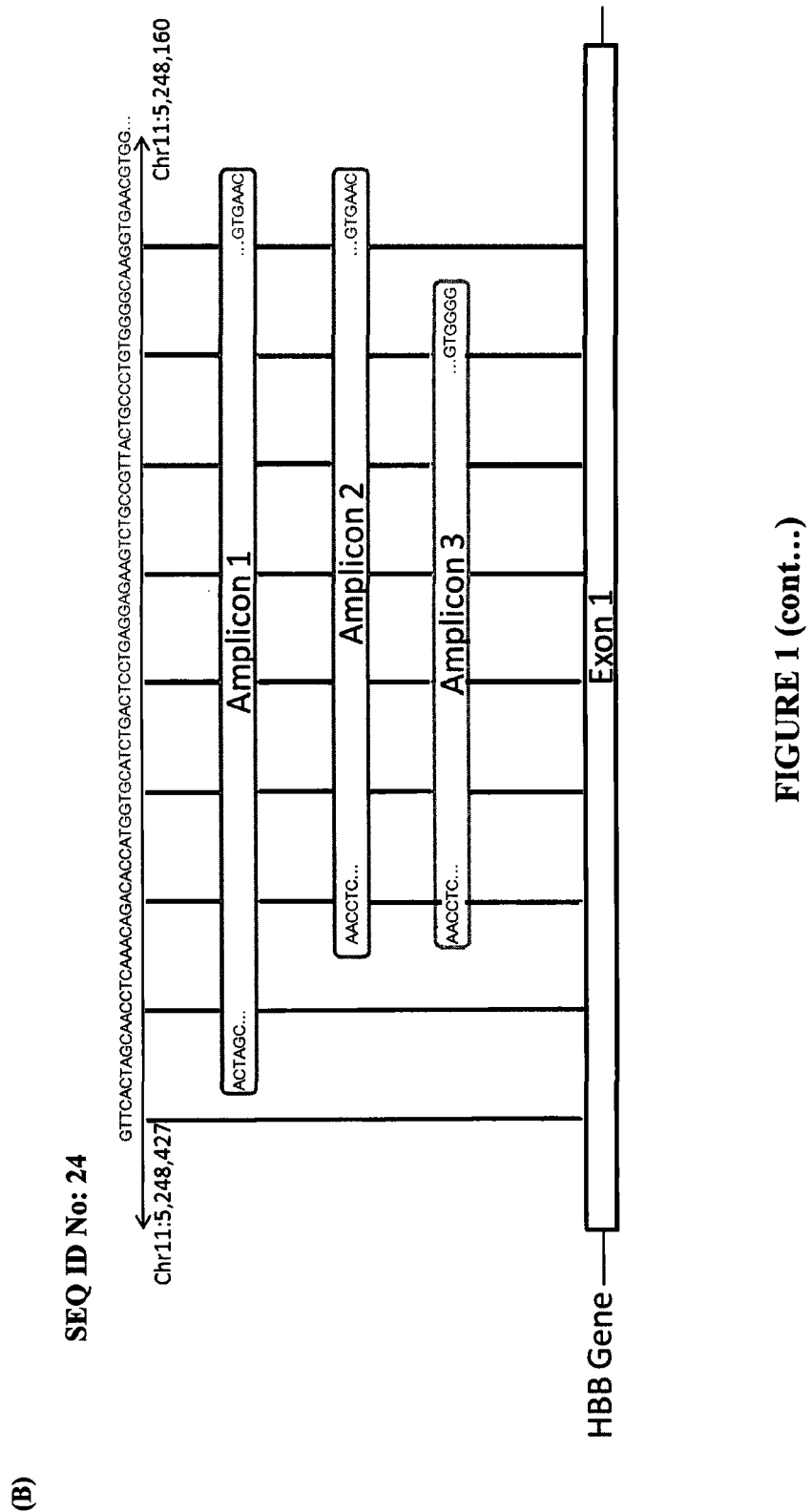
FIGURE 1 (cont...)

(A)

(B)

(B)

SEQ ID No: 31

ACTAGCAACCTCAAACAGACACCAT|GGTGCATCTGACTCCTGAGGAGAAGTCTGC|CGTTACTGCCCTGTGGGCAAGGTGAACA
(Mutant)                                    C          AT SEQ ID No: 32  GGTGCATCTGACTCCTGAGGAGAAGTCTGC
         33    GGTGCACCTGACTCCTGAGGAGAAGTCTGC
         34    GGTGCATCTGACTCCTAAGGAGAAGTCTGC
         35    GGTGCACCTGACTCCTAAGGAGAAGTCTGC
         36    GGTGCATCTGACTCCTGTGGAGAAGTCTGC
         37    GGTGCACCTGACTCCTGTGGAGAAGTCTGC
         38    GGTGCATCTGACTCCTATGGAGAAGTCTGC
         39    GGTGCACCTGACTCCTATGGAGAAGTCTGC FIGURE 3 (Cont...)

(B)
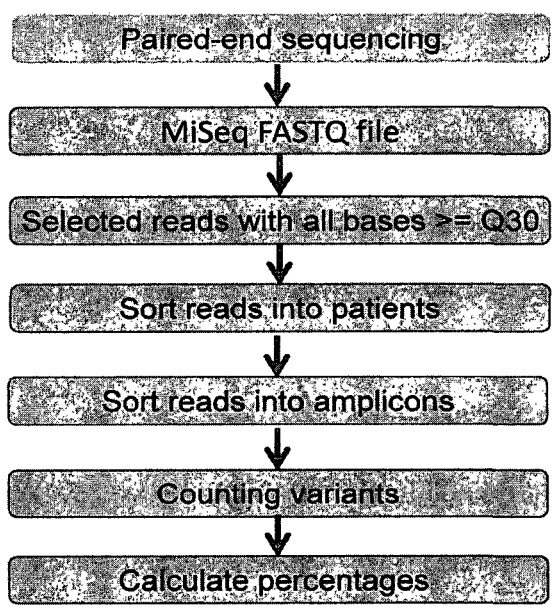
FIGURE 5 (cont...)

Sort reads into amplicons

- Look in Read 1 for 2bp amplicon ID tag
  1. Amplicon 1 starts with an AC
  2. Amplicon 2 ends with a TC
  3. Amplicon 3 ends with an AC Amplicon 1                                                                                                      SEQ ID No: 31
A<u>CT</u>AGCAACCTCAAACAGACACCATGGTGCA<u>T</u>CTGACTCCT<u>GA</u>GGAGAAGTCTGCCGTTACTGCCCTGTGGGCAAGGTGAACA Amplicon 2                                                                                                      SEQ ID No: 40
GCAACCTCAAACAGACACCATGGTGCA<u>T</u>CTGACTCCT<u>GA</u>GGAGAAGTCTGCCGTTACTGCCCTGTGGGCAAGGTGAACAGA<u>TC</u>

Amplicon 3                                                                                                      SEQ ID No: 41
GCAACCTCAAACAGACACCATGGTGCA<u>T</u>CTGACTCCT<u>GA</u>GGAGAAGTCTGCCGTTACTGCCCTGTGGGAGATCGGAAGAGCAC

FIGURE 6

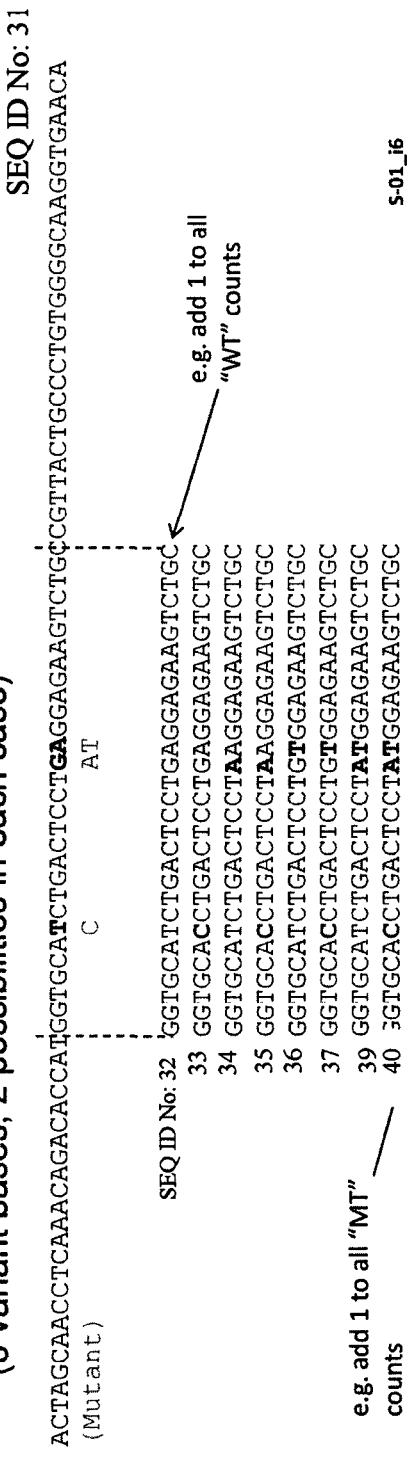
FIGURE 6 (Cont...)

NON-INVASIVE PRENATAL SCREENING

CROSS REFERENCE TO RELATED APPLICATIONS

This application is a national stage application under 35 U.S.C. 371 and claims the benefit of PCT Application No. PCT/GB2014/050810 having an international filing date of Mar. 14, 2014, which designated the United States, which PCT application claimed the benefit of Great Britain Application No. 1304810.3 filed Mar. 15, 2013, the disclosures of each of which are incorporated herein by reference.

REFERENCE TO SEQUENCE LISTING

This application contains a Sequence Listing submitted as an electronic text file named "PCT_GB2014050810_Sequence_Listing_ST25.txt", having a size in bytes of 10KB, and created on Mar. 14, 2014. The information contained in this electronic file is hereby incorporated by reference in its entirety pursuant to 37 CFR § 1.52(e)(5).

FIELD OF THE INVENTION

The present invention relates to methods for screening for genetic disorders and in particular to non-invasive prenatal screening.

BACKGROUND TO THE INVENTION

Prenatal diagnosis offers couples the possibility of identifying genetic disorders. There are a variety of methods for performing such screening, some invasive, others non-invasive, though non-invasive methods are presently limited. One non-invasive approach is to use circulating cell free fetal DNA (ccffDNA) in maternal plasma, which originates from trophoblastic cells and constitutes 5-15% of total plasma DNA. However, the disorders which ccffDNA is used for diagnosis are limited to those with particular characteristics that make diagnosis easier.

For instance, the use of ccffDNA for purposes such as fetal sex determination and fetal Rhesus typing relies on identification of alleles which have been paternally inherited by the fetus and are therefore not present in the mother, making screening for such disorders far simpler. The development of new approaches to allow screening for other disorders using ccffDNA is important, amongst those disorders where there is a need to provide improved prenatal diagnosis for are recessive disorders, particularly those where the underlying mutations are small alterations, rather than large scale chromosomal rearrangements or trisomies. For example, in some cases both the father and mother will be carriers for the same recessive point mutation, making prenatal screening particularly difficult.

Prenatal screening is most commonly performed for particularly severe disorders, amongst such disorders is sickle cell anemia. Sickle cell disease is the most common single gene disorder in the world. It remains most prevalent in Africa and the Middle East, but recent immigrations mean that it is now a significant health issue in the UK population, with a birth incidence of 1:2,400. In 2004 the UK commenced a universal antenatal screening program with the purpose of identifying and helping couples at risk of having a child affected with sickle cell disease. Currently couples opting to have prenatal diagnosis are offered fetal testing by the invasive methods such as amniocentesis and chorionic villus sampling.

Sickle cell disease is now the most common indication for this type of prenatal diagnosis in the UK, with approximately 420 procedures carried out annually. However these procedures carry a risk to the fetus which is unacceptable for some couples and so the development of non-invasive procedures is important.

SUMMARY OF THE INVENTION

The present invention provides a method of prenatal screening comprising:
 (a) amplifying a region encompassing the site of a mutation responsible for the disorder, the amplification being performed on a DNA sample obtained from a pregnant female which comprises both maternal and fetal DNA; and
 (b) sequencing a plurality of products from the amplification and determining whether or not the mutant allele is represented at a different frequency to that expected from the genotype of the pregnant female alone.

The invention also provides a primer:
 (a) selected from the group consisting of a primer comprising the sequence of SEQ ID No:1, SEQ ID No: 2, SEQ ID No: 3, SEQ ID No:4, a primer comprising the sequence of any of SEQ ID NOs: 1 to 4 and a primer with at least 90% sequence identity to any of the preceding primers;
 (b) selected from the group consisting of a primer comprising the sequence of SEQ ID No:10 to 15, a primer comprising the sequence of any of SEQ ID NOs: 10 to 15 and a primer with at least 90% sequence identity to any of the preceding primers; or
 (c) selected from the group consisting of; (i) a primer comprising the sequence of any of SEQ ID Nos: 11, 13 or 15, but where an index sequence is inserted between nucleotides 24 and 25 of the sequence of SEQ ID Nos: 11, 13 or 15; (ii) a primer comprising a primer sequence of (i); or (iii) a primer with at least 90% sequence identity to any of the preceding primers.

The invention further provides a set of primers comprising:
 (a) at least three primer pairs, where each primer pair amplifies a region encompassing a mutation responsible for a disorder; and
 (b) at least three further primer pairs, where each of the primer pairs can amplify one of the amplicons generated by the primer pairs of (a) but also add additional sequences not present in the template.

The present invention additionally provides a set of primers comprising at least four primers of the invention, where the primers are capable of amplifying three amplicons from the beta globin gene encompassing the HbS mutation site.

The invention additionally provides a kit comprising: (a) a primer set of the invention; and
(b) instructions for performing the method of the invention.

BRIEF DESCRIPTION OF THE FIGURES

FIG. 6: Provides a further illustrative summary of how the data obtained in the exemplified method for sickle cell anaemia was obtained.

DETAILED DESCRIPTION

Figure 1:
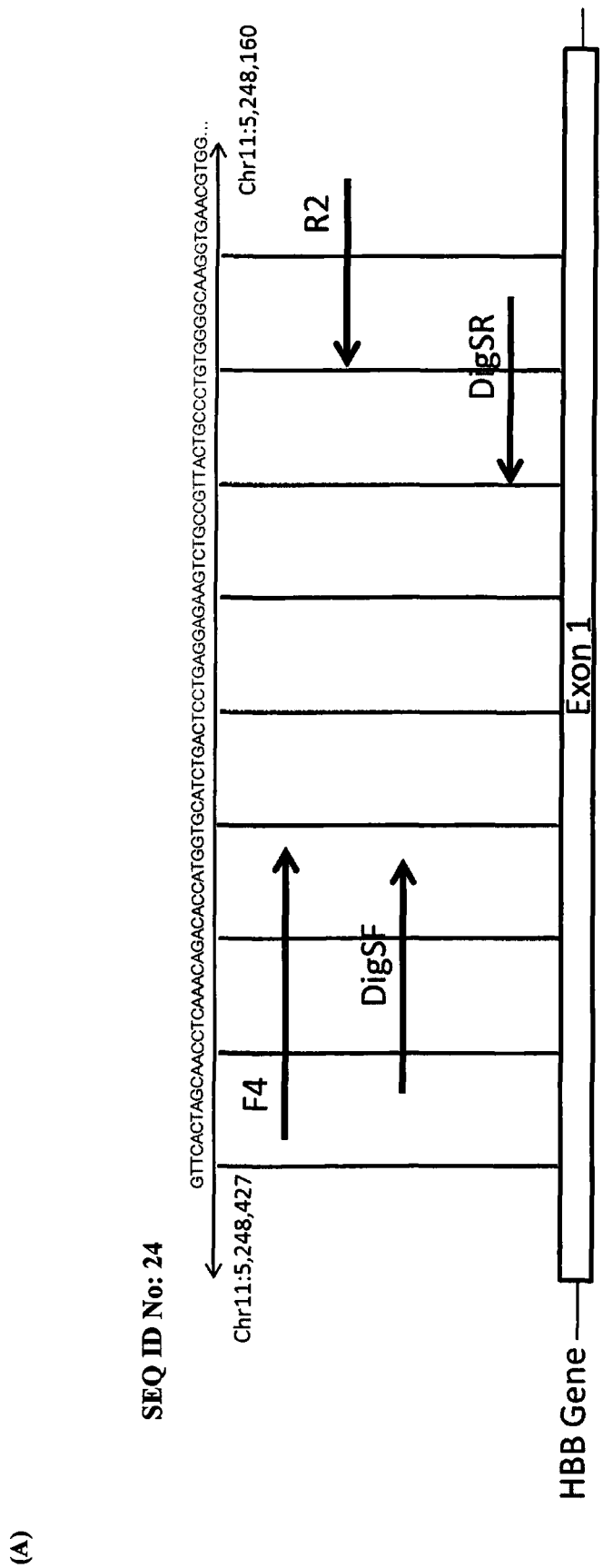
FIG. 1: Panel (A) shows the location of primer pairs employed in the Examples relative to Exon 1 of the HBB gene. Panel (B) shows the three amplicons resulting from amplification.

The present invention provides methods for prenatal diagnosis and in particular for non-invasive prenatal diagnosis (NIPD). In a preferred instance, the methods are used in screening for recessive disorders and/or point mutations.

In one particularly preferred instance, the method comprises measuring the wild-type to mutant allelic ratio, typically by assessing samples containing both fetal and maternal DNA and looking for divergence from the ratio that would be expected from maternal DNA alone. For example, an affected fetus can be distinguished from a fetus which is a heterozygous carrier by measuring the deviation from a 1:1 allelic ratio that is produced by over representation of the mutant allele where the fetus has the disorder.

Disorders & Mutations

The invention may be employed to screen for any suitable genetic disorder or disease. In one preferred instance, the disorder to be screened for is a recessive disorder. In one preferred instance, the disorder screened for may be a sickle cell disease and in an especially preferred instance, the disorder may be sickle cell anemia.

In one instance, the invention will be employed where both parents are known to be carriers for the same recessive disorder, particularly where both parents carry the same mutation for the disorder. The parents may have already had a child affected by the disorder. For example, one or both of the parents may come from a family whose pedigree is known to include relative(s) with the disorder. The parents may come from a group known to have a high incidence of the condition, for the instance in the case of sickle cell anemia the parents may be of African origin and in the case of Tay-Sachs syndrome the parents may be of Ashkenaki Jewish origin.

The invention is particularly applicable where the condition being screened for is a severe one. A preferred disorder that the invention may be used to screen for is a Thalassemia. In an especially preferred instance the disorder is sickle cell anemia. In a further instance, the disorder is Cystic Fibrosis. In another preferred instance, the disorder is Tay-Sachs syndrome. In another instance, the disorder is automsomal recessive polycystic kidney disease (ARPKD). In a further instance, the disorder is Spinal Muscular Atrophy (SMA). In a further instance, the disorder is Muscular Dystopy. In one instance, the disorder is a blood disorder and may be, for instance, a Hemostasis. In one case, the disorder is a Haemophilia. Examples of Haemphilia which may be detected include Haemophilia A and Haemophilia B.

Other disorders which may be detected include disorders of Lipid Metabolism, Peroxisomal and Mitochondrial fatty acid oxidation deficiencies, mucopolysaccharidoses, disorders of amino acid and related compounds metabolism, disorders of carbohydrate metabolism, congenital adrenal hyperplasia, primary immunodeficiency diseases, and disorders of bone and connective tissue (including, for instance, osteogenesis imperfecta).

The invention may be applied to any suitable mutation. In one preferred instance, the mutation screened for is a point mutation, particularly a point mutation which is responsible for a recessive condition. In one instance, the mutation may therefore be a base substitution, for instance the mutation may be a single base mutation, preferably a single base substitution. In another instance, the mutation may be a deletion, for example a deletion of under 100 bp, under 75 bp, under 50 bp, under 40 bp, under 30 bp, under 20 bp, under 10, 9, 8, 7 or 6 bases in size. The deletion may be, in some instances, 5, 4, 3, 2, or 1 bases in size and in one preferred instance is a single base deletion. The mutation may also be an inversion, for instance of any of the sizes specified. The mutation may be a duplication, for instance, a duplication of any such lengths. The mutation may, for instance, in some cases (a) bring about an amino acid change, (b) result in a stop codon causing premature translation, or (c) result in a change in RNA splicing.

In a preferred instance, the mutation may be that responsible for the disease. In other instances, the mutation or polymorphism may be one closely linked to the disease mutation, for instance in linkage disequilibrium with the disease mutation. In one instance, the genetic marker being used is a SNP associated with the disorder. Any suitable SNP known to be associated with the disease being screened for may be employed. Hence, in some cases, the sequence change being screened for is a polymorphism which is not responsible itself for the disorder.

In one preferred instance, the condition being screened for is one where a particular mutation associated or causing the disease is found in a significant proportion of sufferers, for instance a particular mutation is found in at least 5%, 10%, 25%, 50%, 75%, 85% or more of the sufferers. It may be that both parents have been identified as carriers for that specific mutation. Part of the method of the invention may comprise identifying the mutation carried by the parents, or the method may be performed on individuals where the mutation they carry has already been identified.

In a particularly preferred instance, the mutation is the most common sickle cell anemia mutation and so is a single change from A to T in the sixth codon of the beta-globin gene which results in a glutamic amino acid being substituted by valine. Hence, in such instances, the method may be used to screen for sickle cell anemia and determine whether the fetus is homozygous for that mutation.

Another example of a particularly preferred mutation which may be screened for is the Hb C mutation, which is a G to A sequence change in the sixth codon of the beta-globin gene which results in a glutamic amino acid being substituted by Lysine.

In one instance, the method may be used to screen for both the sickle cell anemia mutation and the Hb C mutation.

DNA Samples

The methods of the invention are typically performed on a maternal sample, that is a sample obtained from a pregnant subject. Hence, in an especially preferred instance, the method is performed on a sample from a pregnant woman, so the sample is human, though the method may also be performed on a pregnant non-human animal. The method is preferably performed on DNA collected using a non-invasive approach.

In one instance, the sample taken is a blood sample, a urine sample, a stool sample or a saliva sample. Preferred examples of samples include, blood, urine and saliva samples. In an especially preferred method the sample is a blood sample. Reference to a blood sample includes a whole blood sample, a plasma sample or a serum sample and any of those may be employed.

In one instance, any non-invasive sample comprising DNA molecules representative for the genome of the developing fetus as well as that of the mother may be employed. For instance, the method may preferably be performed using a maternal blood sample and in particular DNA harvested from maternal blood, preferably comprising ccffDNA. In a preferred instance, the sample is obtained by enrichment and quantification of selected cell-free DNA sequences in a maternal blood sample. In an especially preferred instance, the sample is, or comprises, ccffDNA, particularly that extracted from a blood sample taken from the pregnant female.

The method may also be performed on a control sample, for instance a control sample from a pregnant woman where the fetus is known to be homozygous for the disorder being tested for, a carrier or to have a wild type genotype. Control samples produced by mixing a known amount of DNA of a particular genotype with DNA from a carrier also may be employed. For instance, using sickle cell anemia as an example, a control may comprise DNA from a sickle cell carrier mixed with a small amount of DNA from (a) an individual with sickle cell anemia; (b) an individual who is a carrier for sickle cell anemia; or (c) a wild type individual. For instance, 5% or less of the DNA from (a), (b) or (c) may be present in one instance. By using such samples it is possible to mimic the mixture of maternal and fetal DNA which will be found in test samples and so provide a control. Such an approach may be employed for any disorder being screened for. Such controls may be present in the kits of the invention.

Sample Preparation

In order to help optimize results, sample preparation may be preferably performed in a particular way, particularly where the sample comprises, or is, ccffDNA, as ccffDNA may be subject to degradation.

In one instance, samples are treated quickly to help avoid DNA degradation and in particular ccffDNA degradation. Hence, in a preferred instance, the sample is processed ready for analysis within 24 hours of being obtained, for instance, within 20 hours, 18 hours, 16 hours, 12 hours, 8 hours, 7 hours, 6 hours, 5 hours, 4 hours, 3 hours, 2 hours or 1 hour. In one particularly preferred instance, the sample is processed within about 7 hours and in particular within about 6 hours. It may be that the sample is not immediately analyzed, but is stored under conditions that prevent or minimize further degradation of the sample, for instance by freezing the sample, such as at −80° C.

In a preferred embodiment, blood will be the sample obtained from the patient and in an especially preferred instance, the blood sample will be spun down and plasma separated from the cellular fraction within any of the time periods specified above, particularly within about 8 hours, preferably within about 7 hours and more preferably within about 6 hours. For instance, the blood may be centrifuged, with the plasma being then separated and frozen, in a preferred instance the blood sample is centrifuged, plasma separated, the plasma respun and then the plasma then again separated, preferably the sample is then frozen. Such an approach may be optionally employed in any of the embodiments discussed herein and preferably is so.

Alternatively, or additionally, samples may be collected in a way that helps prevent or reduce nucleic acid degradation and in particular degradation of cell free nucleic acids. For instance, blood samples may be collected in receptacles that help prevent nucleic acid degradation and in particular degradation of cell free nucleic acids in samples. Such vessels may comprise a preservative that inhibits nucleic acid degradation, an inhibitor of metabolism and/or an inhibitor of an enzyme responsible for nucleic acid degradation. Examples of such vessels include those of Streck which inhibit nucleic acid degradation of cell free DNA.

In one preferred instance, the sample, particularly a blood sample, is processed in one of the above specified time periods and using a receptacle which inhibits or reduces nucleic acid degradation, particularly degradation of cell free nucleic acids.

Once a sample has been prepared and processed, preferably DNA is then extracted. In one preferred instance, where a sample has been frozen, DNA is extracted immediately after the sample is defrosted. Any suitable DNA extraction technique may be employed to obtain the DNA for analysis. In one preferred instance, DNA is extracted using a QIAmp circulating Nucleic Acid Kit.

In a particularly preferred instance, the DNA sample is analyzed to confirm the presence of fetal DNA. That may particularly be the case where a sample comprising ccffDNA is being employed, because of the possibility of degradation of the sample, particularly if not spun down quickly enough. Analysis for the presence of a fetal marker to confirm the presence of fetal DNA may be performed separately or as part of the method of the invention. Any suitable marker may be analyzed to confirm the presence of fetal DNA in the sample, with one instance of a possible marker being the RASSF1A marker.

In one preferred instance, the marker employed to detect fetal DNA is any suitable single nucleotide polymorphisms (SNPs) that the fetus has inherited from the father which is not present in the mother. In the case of a male fetus the Y chromosome can be used, as maternal DNA will lack any Y chromosome sequences, so the presence of any Y chromosome sequence can be used to confirm the presence of fetal DNA and/or to quantify the amount of fetal DNA. In other instances polymorphic short tandem repeats, SNPs and/or indel markers may be employed, such as a panel of any of those markers.

In a further preferred instance, the amount of DNA present in the sample may be quantified. The method may quantify the amount of fetal DNA present. For instance, the amount of DNA present may be quantified by PCR, for example by real time PCR or any other suitable technique, and such an approach may be used to quantify the amount of fetal DNA using any of the fetal DNA markers discussed herein. In one instance, the method employed to quantify the amount of fetal DNA may be that described in White et al (2012), *Evaluation of a Novel Assay for Detection of the Fetal Marker RASSF1A: Facilitating Improved Diagnostic Reliability of Noninvasive Prenatal Diagnosis*. PLoS ONE 7(9): e45073. doi:10.1371/journal.pone.0045073, the entirety of which is incorporated by reference, including the specific method described.

Hence, any of the methods of the invention may optionally comprise quantification of the amount of fetal DNA present.

Overall therefore, preferred embodiments of the invention may in some cases include: (a) the sample comprising ccffDNA; (b) the sample being processed within eight hours, particularly about seven hours and more particularly within about six hours; and/or (c) the presence of fetal DNA being confirmed and in particular the amount being quantified. In some instances, for example, both (a) and (b) will apply, in others all of (a) to (c) will be preferably employed.

In further preferred embodiments, the invention may in some cases include: (a) the sample comprising ccffDNA; (b) the sample being treated to prevent DNA breakdown, for instance by using collection vessels that inhibit such degradation; and/or (c) the presence of fetal DNA being confirmed and in particular the amount being quantified. In some instances, for example, both (a) and (b) will apply, in others all of (a) to (c) will be preferably employed.

In further preferred embodiments of the invention may in some cases include: (a) the sample comprising ccffDNA; (b) the sample being processed within eight hours, particularly about seven hours and more particularly within about six hours and/or the sample being treated to prevent DNA breakdown, for instance by using collection vessels that inhibit such degradation; and/or (c) the presence of fetal DNA being confirmed and in particular the amount being quantified. In some instances, for example, both (a) and (b) will apply, in others all of (a) to (c) will be preferably employed.

Primers & Amplicons

Any suitable primer pairs may be employed in the invention. In one instance, an amplicon is chosen to be amplified and primer pairs designed accordingly. In a particularly preferred instance, the amplification will result in a population of amplification products that is representative of the starting template DNA, in particular in reference to the incidence of maternal and fetal template molecules within the original sample.

Typically, the amplicon will comprise the site of the mutation or mutations being assessed. By sequencing the PCR product it is then typically possible to determine the representation of particular alleles for the region in the PCR product and so in the original sample. By determining divergence from what would be expected for the maternal genotype, it is typically possible to identify the contribution of the fetal DNA in the sample and so typically whether the fetus has the disorder screened for. In a preferred instance, the genotype of the fetus for the disorder may be determined.

For instance, taking the case of sickle cell anemia as an illustrative example:

both parents will be carriers for the sickle cell allele, so the maternal DNA on its own, with no fetal DNA, should have a ratio of 1:1 for the wild type and mutant alleles;

if the fetus is also a carrier for sickle cell anemia, then the presence of fetal DNA will not alter the ratio of wild type and mutant alleles in the sample, because the fetus has the same genotype as the mother;

if the fetus has sickle cell anemia, the fetus is homozygous for the mutant allele and the presence of fetal DNA in the maternal sample will mean that the mutant allele should be found to be over-represented in comparison to what would be expected from maternal DNA on its own; and conversely, if the fetus is wild type, the presence of fetal DNA will mean that the wild type allele will be over-represented compared to what would be expected from maternal DNA alone.

In a preferred instance, more than one amplicon will be amplified. For instance, there may be a plurality of amplicons and in particular overlapping amplicons where each amplicon comprises the mutation sites. By adopting such a strategy the different amplicons can be used to confirm further the result given by the other amplicons. In one instance, two, three, four, five, six or seven amplicons may be amplified or at least such numbers. In a preferred instance, three, four or five amplicons may be amplified and in particular three amplicons.

In one instance, a single amplicon is amplified using a primer pair, but more than once. Hence, the same amplicon may be amplified in parallel in separate reactions. For instance, the same amplicon may be amplified in duplicate, triplicate, four times, or more. It may be that such parallel amplifications are performed as a way to further confirm the results seen. In a preferred instance, the same amplicon is amplified in triplicate in separate reactions.

In another instance, more than one amplicon may be chosen with different amplicons encompassing different mutation sites. It may be that multiple amplicons are chosen to allow screening for more than one mutation and/or for more than one disorder, preferably at the same time. In such instances, it may be that for each mutation and/or disorder there are overlapping amplicons as described above.

In a preferred instance, it may be that the amplicon is under 500 bp in length, for instance, under 400 bp, 300 bp, 250 bp, 200 bp or 150 bp in length, in some cases under 140 bp, 130 bp, 125 bp or 120 bp in length. It may be that the amplicon is under 110 bp, 100 bp, or 90 bp in length. In some cases all the amplicons will be under such length.

In a particularly preferred instance, more than one primer pair may be employed for each amplicon. For instance, a first primer pair may be used to perform an initial amplification of the amplicon, then a second primer pair may be employed to amplify the amplicon further. Such a two step approach may help ensure that the allelic frequency is as close as possible in the end PCR product of that in the original template. It may be that the second primer pair employed in the second amplification introduces additional sequences to those amplified from the template. For instance, the second primer set may introduce additional sequences to help facilitate analysis of the sequence data obtained.

In one instance, at least one of the primers includes a sequence unique to each amplicon to allow products from each amplicon to be distinguished. In one case, the primers for the second PCR have specific adaptors for cluster generation. In another instance, the primers for the second amplification have a binding site for a sequencing primer. In a further instance, at least one of the primers comprises the sequences for cluster generation as well as the sequence for the sequencing primer, in some cases all of the primers do so. In a particularly preferred instance, at least one, and preferably all, of the primers for the second amplification have Illumina specific adaptors.

In a further preferred embodiment, at least one of the primers in each pair comprises a "bar code" or index sequence allowing identification of a specific amplicon. By providing the same primer pair, but with different "bar code" sequences present, it is also possible to allocate a particular bar code to a particular patient and then analyze the samples from the different patients simultaneously, because the results for each patient are denoted by a particular bar code. It is also possible to have a bar code where one part of the sequence is unique to the amplicon, the other denoting which patient the bar code comes from. Such an approach may allow pooling of samples for sequencing.

In one case, where the invention is employed to screen for sickle cell anemia, at least one and preferably all the amplicons are located in exon 1 of the beta-globin gene. In one preferred instance, one or more of the following primers may be employed in the invention for use in screening for sickle cell anemia:

```
                                            (SEQ ID No: 1)
872_HBS_F4-"ACTAGCAACCTCAAACAGACACCATG";

(SEQ ID No: 2)
875_HBS_R2-"GTTCACCTTGCCCCACAGGGCAGTA"

(SEQ ID No: 3)
879_digSickleF-"GCAACCTCAAACAGACACCAT"

(SEQ ID No: 4)
880_disgSickleR-"CCCCACAGGGCAGTAACG".
```

It may be that a primer comprising one of the above sequences is employed, or in other instances a primer consisting of the above sequence may be employed. In other instances, a primer with at least 90%, 91%, 92%, 93%, 94%, 95%, 96%, 97%, 98% or 99% sequence identity to one of the above primers may be employed. In some cases, a primer with not more than five, four, three, two or one base sequence changes in comparison to one of the above primers may be employed.

In a preferred instance, one or more of the following primer pairs may be employed:
Set 1: 872_HBS_F4(SEQ ID No: 1)+875_HBS_R2 (SEQ ID No: 2)
Set 2: 879_digSickleF (SEQ ID No: 3)+875_HBS_R2 (SEQ ID No:2)
Set 3: 879_digSickleF (SEQ ID No: 3)+880_disgSickleR (SEQ ID No: 4)

In a particularly preferred instance, the four primers for the above three primer pairs are all employed in the invention.

Further primer pairs corresponding to the above pairs, but with any of the levels of sequence identity or sequence changes may be employed. For instance, rather than a primer of sequence of SEQ ID No:1, a primer comprising such a sequence may be employed in the primer pair, or a primer with one of the above specified levels of sequence identity or a primer with one of the above level of sequence changes and that also applies to the other primers.

The invention also provides a set of primers comprising at least one of the pairs of the above primers, preferably at least three of the above primers and more preferably all four of the primers. Hence, it one preferred instance, the invention provides a set of primers comprising, or consisting of, the primers referred to above.

The invention also provides a kit comprising: (a) a primer set of the invention; and (b) instructions for performing the method of the invention.

In a preferred instance, the above referred to primers are used in the initial amplification.

In a further preferred instance, the second amplification is performed using primers based on the primers used in the first amplification, but with the additional sequences to help identify the amplicons and/or the analysis of the data harvested. In one instance, at least one of the primers in each primer pair will include an "Index sequence" to allow identification of the amplicon from that pairing. Any suitable index sequence may be employed, for instance, illustrative examples of possible index sequences include:

```
                                            (SEQ ID No: 5)
                    Index6: ATTGGC (SEQ ID No: 6)
                    Index12: TACAAG (SEQ ID No: 7)
                    Index4: TGGTCA (SEQ ID No: 8)
                    Index5: CACTGT (SEQ ID No: 9)
                    Index7: GATCTG
```

In one instance, the above indexes are used in the indicated order, i.e. Index 6, Index 12, Index 4, Index 5 and Index 7.

Examples of forward and reverse primers that may be employed in the second PCR are presented below:
Primer Sequence for 2$^{nd}$ Amplification:
Amplicon 1:

```
F4_seq
                                           (SEQ ID No: 10)
AATGATACGGCGACCACCGAGATCTACACTCTTTCCCTACACGACGCTC TTCCGATCT
R2_seq
```

A primer comprising SEQ ID No: 16 joined by an index sequence to SEQ ID No: 17, with SEQ ID Nos: 16 and 17 having the following sequences:

```
                                           [SEQ ID NO: 16]
CAAGCAGAAGACGGCATACGAGAT

[SEQ ID NO: 17]
GTGACTGGAGTTCAGACGTGTGCTCTTCCGATCTGTTCACCTTGCCCCAC

AGGGCAGTA.
```

The primer hence having the formula SEQ ID NO:16-INDEX-SEQ ID NO:17, where INDEX is the Index Sequence. The primer hence having the sequence

```
                                           (SEQ ID No: 11)
CAAGCAGAAGACGGCATACGAGATGTGACTGGAGTTCAGACGTGTGCTCTT

CCGATCTGTTCACCTTGCCCCACAGGGCAGTA,
``` but with an index sequence inserted between nucleotides 24 and 25 of that sequence.
Amplicon 2:

```
digSF_seq
                                           (SEQ ID No: 12)
AATGATACGGCGACCACCGAGATCTACACTCTTTCCCTACACGACGCTC TTCCGATCT.
R2_seq
```

A primer comprising SEQ ID No: 18 joined by an index sequence to SEQ ID No: 19, with SEQ ID Nos: 18 and 19 having the following sequences:

[SEQ ID NO: 18]
CAAGCAGAAGACGGCATACGAGAT

[SEQ ID NO: 19]
GTGACTGGAGTTCAGACGTGTGCTCTTCCGATCTGTTCACCTTGCCCCAC
AGGGCAGTA.

The primer hence having the formula SEQ ID NO:18-INDEX-SEQ ID NO:19, where INDEX is the Index Sequence. The primer hence having the sequence (SEQ ID No: 13)
CAAGCAGAAGACGGCATACGAGATGTGACTGGAGTTCAGACGTGTGCTCT
TCCGATCTGTTCACCTTGCCCCACAGGGCAGTA, but with an index sequence inserted between nucleotides 24 and 25 of that sequence.
Amplicon 3:

digSF_seq
(SEQ ID No: 14)
AATGATACGGCGACCACCGAGATCTACACTCTTTCCCTACACGACGCTC
TTCCGATCT:::::::::::::::::::::::::.
digSR_seq A primer comprising SEQ ID No: 20 joined by an index sequence to SEQ ID No: 21, with SEQ ID Nos: 20 and 21 having the following sequences:

[SEQ ID NO: 20]
CAAGCAGAAGACGGCATACGAGAT

[SEQ ID NO: 21]
GTGACTGGAGTTCAGACGTGTGCTCTTCCGATCTCCCCACAGGGCAGTAA
CG.

The primer hence having the formula SEQ ID NO:20-INDEX-SEQ ID NO:21, where INDEX is the Index Sequence. The primer hence having the sequence (SEQ ID No: 15)
CAAGCAGAAGACGGCATACGAGATGTGACTGGAGTTCAGACGTGTGCTCT
TCCGATCTCCCCACAGGGCAGTAACG, but with an index sequence inserted between nucleotides 24 and 25 of that sequence.

Also provided are primers with any of the above specified levels of sequence identity to: (a) SEQ ID No: 10; (b) SEQ ID NO:16-INDEX-SEQ ID NO:17; (c) SEQ ID No: 12; (d) SEQ ID NO:18-INDEX-SEQ ID NO:19; (e) SEQ ID NO 14; or (f) SEQ ID NO:20-INDEX-SEQ ID NO:21. In respect of the primer SEQ ID NO:16-INDEX-SEQ ID NO:17, the invention provides the primer with any suitable sequence as the index sequence (INDEX), including all permutations of the primer including the above mentioned index sequence, i.e SEQ ID NO:16-INDEX-SEQ ID NO:17 where the index sequence is any one of Index 6, Index 12, Index 4, Index 5 or Index 7, as well as primers with the above specified levels of sequence identity and/or sequence changes to such primers. The invention also provides such primers for SEQ ID NO:18-INDEX-SEQ ID NO:19 and SEQ ID NO:20-INDEX-SEQ ID NO:21.

The invention also provides a set of primers comprising primers with the sequence of SEQ ID NO:18-INDEX-SEQ ID NO:19, but with a primer for each permutation of at least five different index sequences. The invention also provides such primers for each of the primers (a) SEQ ID NO:17-INDEX-SEQ ID NO:18; (b) SEQ ID NO:19-INDEX-SEQ ID NO:20; and (c) SEQ ID NO:20-INDEX-SEQ ID NO:21. Any of the primers discussed herein may be provided with an index sequence, such as any of the specific index sequences discussed herein. The specific adaptors, indexes and/or sequence binding sites discussed herein, including the specific ones, may be present in the primers used for the second PCR. For instance, such sequences may be employed where the second PCR is for a different condition to sickle cell and hence different amplicons are being employed.

In a preferred instance, the primers for the second PCR comprise the sequence of the primers for the first PCR, plus such additional sequences, for instance added as shown for the specific primers discussed herein.

Any of the primer sets discussed herein and kits may comprise the primers for each permutation of a primer with a plurality of index sequences and in particular the index sequences discussed herein.

Amplification

In a preferred method of the invention, an amplification method is used to amplify from the maternal sample to produce the nucleic acid for eventual sequencing. In a particularly preferred instance, the amplification method employed is PCR. In one instance, the PCR employed is not a digital PCR.

As discussed above, in a particularly preferred instance, a two-step PCR is performed. For instance, a first PCR is performed with the initial primer pairs and then a sample of the amplification product is used as the template for a second amplification with the second primer pairs. In a further preferred instance, the first PCR is performed with a relatively low number of cycles, for example with under 25, 20, 19, 18, 17, 16 or 15 cycles, preferably with 16, 17 or 18 cycles and in particular with 17 cycles. In one case, the initial PCR may have from 15 to 20 cycles, preferably from 16 to 19 cycles, more preferably 17 or 18 cycles.

The second PCR may in some instances be performed with the same or a different number of cycles to the first amplification, for example in one case the second PCR may be performed with a higher number of cycles than the first PCR, such as with, for instance, 30, 29, 28, 27, 26, 25, 24, 23, 22, 21 or 20 cycles. In one instance, the second PCR may have from 20 to 30 cycles, preferably from 22 to 28 cycles and in particular from 24 to 26 cycles. In one preferred instance, any combination of the numbers of cycles for the initial PCR and second PCR specified above may be employed, for example in one case the initial PCR has from 15 to 20 cycles and the second PCR from 20 to 30 cycles, in a preferred instance, the initial PCR may have from 16 to 18 cycles and the second PCR from 23 to 27 cycles.

Preferably the first and second PCR will be designed with the aim of the end amplification product being as representative as possible of the initial sample, particularly in terms of the ratio of maternal DNA to fetal DNA. As discussed herein, additional analysis, such as the use of a fetal specific marker, may also be employed to confirm the presence of fetal DNA.

Any suitable polymerase may be used in the amplification, preferably the polymerase is one with a low error rate. One preferred example of a polymerase which may be employed is Pwo polymerase. For instance, in one case, a final concentration of about 240 nmol/L for each primer and about 0.1 U/µl of Pwo DNA polymerase (Roche) is used in amplification, preferably in both of the two steps of amplification.

Any suitable cycling conditions may be employed in the PCR and the conditions may be tailored to the specific primers employed. In one case the cycles in the initial PCR are from 2 to 4 minutes and preferably 3 minutes, with a temperature of from 90° C. to 98° C., preferably from 92° C. to 96° C. and in particular about 94° C. For instance, in one case the cycling conditions for the primary PCR may be 94° C. for 3 minutes, with any of the above mentioned numbers of cycles being performed and in particular with about 17 cycles being performed.

In another instance, the cycling conditions for the second PCR may be: (a) from 90° C. to 98° C., preferably from 92° C. to 96° C. and in particular about 94° C., for instance from 30 to 60 seconds, preferably from 45 to 50 seconds; followed by (b) from 52° C. to 58° C., preferably from 54° C. to 56° C. to, for instance from 30 to 60 seconds, preferably from 45 to 50 seconds; followed by (c) 68° C. to 76° C., preferably from 70° C. to 74° C., for instance from 45 to 90 seconds, preferably from 50 to 70 seconds. In some cases, any of the above specified number of cycles may be employed in the second PCR, particular from 25 to 30 cycles. In a preferred instance, such conditions are employed with the primers discussed herein for screening for sickle cell anemia.

In one preferred instance, the cycling conditions employed are 94° C. for 3 minutes, then 17 cycles (primary PCR); 25 cycles or 30 cycles of 94° C. for 45 seconds, 56° C. for 45 seconds and 72° C. for 1 minute followed by 72° C. for 10 minutes (secondary PCR). Such conditions are in one instance employed for the sickle cell anemia screening method discussed herein and in particular for the specific primers discussed herein for that purpose, though the cycling conditions may also be employed in general. In one instance, where the method is employed for sickle cell anemia, particularly when using the primers for that discussed herein, in the second PCR 25 cycles are used for Amplicon 3 and 30 cycles for Amplicon 1 and 2 in the secondary PCR.

In one particularly preferred instance, each amplicon may be amplified in separate reactions. For instance, the first and second PCRs for each amplicon may be performed separately to those for the other amplicons. In some cases, the amplicons are amplified together.

Sequencing & Sample Analysis

The methods of the invention preferably comprise sequencing products of the second PCR.

In one instance, after amplification, in particular after both of the first and second PCRs, the sample may be purified to help in subsequent analysis. The sample may be analyzed to help normalize all the samples to the same molarity. For instance, a MinElute PCR purification kit may be used for sample clean-up and/or a 2100 DNA bioanalser kit from Agilent Technologies may be used in the normalization of DNA concentrations in the samples. Any suitable approach though may be employed in such cleanup and normalization.

Samples may be pooled prior to sequencing. For instance, where primers carry an index/bar code specific for an amplicon and/or patient that means that pooled samples may be sequenced together. For instance, all of the amplicons generated may be pooled together and sequenced. In some cases, samples may be pooled from 1 to 10, 2 to 8, 3 to 6 and in particular 5 patient samples. In some instances, all of the amplicons from such numbers of patients may be pooled prior to sequencing.

In a particularly preferred instance of the invention, a control is added to the sample for analysis. For instance, a control library may be added, for instance to increase diversity. In a preferred instance, the control library will be from an organism with a small genome, diverse GC:AT content and/or well defined genome sequence, preferably having at least one of those characteristics, more preferably at least two and still more preferably at least. In one instance, the control library is from a virus, particularly a virus with a small genome, preferably with the above mentioned characteristics. In a preferred instance, the use of a control library helps avoid low diversity sequencing. In an especially preferred instance, the control library is from the PhiX library, an example of a PhiX library which may be employed is that from Illumina, for instance the Illumina PhiX control version 3 with insert size of 425-525 bases. Any suitable library which introduces diversity may though be employed.

In a preferred instance, the method of the invention comprises sequencing a plurality of products from an amplicon. That means that it is typically possible to analyze the incidence of a particular allele or mutation in the sequenced population of PCR products. Preferably by determining divergence from the maternal genotype it is possible to determine if the fetus has a disorder and in particular it is possible to determine the genotype of the fetus. In one instance, at least 100, 500, 1000, 5,000, 10,000 or more products for each amplicon may be sequenced. In some cases the number of products sequenced is at least 100,000, at least 500,000, at least one million, at least two million, at least five million, at least seven million or more. In some cases the number of products sequenced is from about 100,000 to about 15 million, preferably from about 500,000 to about 12 million, more preferably from about one million to ten million products. In some further instances, the number of products sequences is from about one million to about seven million and in particular from about two million to about five million. In some cases up to the above specified numbers are sequenced.

Any suitable sequencing technique may be employed, particularly those that allow simultaneous sequencing of a plurality of molecules, including those that allow high throughput and ultrahigh throughput. In one especially preferred instance, a Next generation Sequencing (NGS) technique is employed to perform the sequencing.

Examples of sequencing techniques which may be employed include:

sequencing by pyrosequencing, for instance the synthesis Roche/454 system;

fluorescence based sequencing, such as Illumina sequencing or Intelligent Biosystems sequencing;

Ion Torrent (H+ ion detection) sequencing;

fluorescence-single molecule sequencing, such as Heliscope sequencing;

DNA Nanoball array with CPAL sequencing (Combinatorial probe anchor ligation);

complete genomics sequencing;
sequencing by ligation, such as SOLiD (based on Polony); and
single Molecule Real time sequencing (SMRT) such as Pac Bio sequencing;
Further examples of possible sequencing approaches which may be employed, include:
electron microscope sequencing—Electron Optica, ZS Genetics;
sequencing by synthesis (recording pH and/or temperature), such as Genapsys sequencing;
Nanopore—biological and solid state—such as the systems of Genia, IBM/Roche, ONT, Nabsys, Noblegen;
sequencing by hybridisation—such as the GnuBio system;
Optical Imaging—such as the Lightspeed Genomics sequencing;
charge detection in a Nanowire—such as the Quantum Dx sequencing;
Atomic force microscopy—such as the Reveo sequencing system; and
sequencing by expansion—such as the Stratos Genomics system.

In one especially preferred embodiment, the sequencing technique is one based in reversible dye-terminators and/or engineered polymerases and in particular is Illumina sequencing. In Illumina sequencing typically single molecules of DNA are attached to a flat surface, amplified in situ and used as templates for synthetic sequencing with fluorescent reversible terminator deoxyribonucleotides. Images of the surface may then be analyzed to generate a sequence.

In a further preferred instance, a bench top sequencer is employed and in particular one which performs NGS and preferably one that performs Illumina sequencing. Illustrative examples of sequencers which may be employed include the HiSeq 2500/1500, HiSeq 2000/1000, the Illumina Genome Analyzer and the Illumina Miseq. Any suitable sequencer may be employed.

Preferably, the sequencing employed is subgenomic, in particular the sequencing is typically restricted to the amplicons or regions within the amplicon and so preferably only a relatively small region encompassing the mutation site is sequenced rather than sequencing large lengths of sequence. By focusing the sequencing on specific regions in such embodiments the overall approach is typically cheaper and also more accessible to a greater range of laboratories, rather than only being available in a few specialist establishments. For instance, the length of the region sequenced may be, for example, any of the lengths specified herein, in one case the size of the region sequenced may be under 700 bp, 600 bp, 500 bp, 400 bp or 300 bp. In some cases, the size of the region sequenced is under 250 bp, 200 bp, 150, 125 bp, 100 bp or 90 bp. The size of the sequenced region may though vary, for example if the mutations being looked for are spread-out over a longer distance, though in some instances multiple amplicons may be employed to cover the relevant regions of the gene, for example where there are a small number of different mutations to be screened for. The overall length covered by the amplicons and hence the region sequence, may be, in some instances, under 500 bp, under 400 bp, under 250 bp, under 200 bp in length or under any of the other lengths specified herein.

The sequence data obtained is analyzed by any suitable technique. For instance, the analysis will typically allow sequences to be assigned to a particular amplicon and/or patient, the overall ratio of sequences within each amplicon may then be determined.

For instance, Perl script may be employed to analyze the data. The index sequences may be used to sort pair-end reads into samples, the index sequences/bar codes may also be used to sort them into amplicons and/or specific patients. By way of illustration, in the method for sickle cell anemia exemplified the indexes are used to sort each paired-end reads into samples, then using the 2 bp amplicon ID tag the reads were divided into the 3 amplicons, based on the following rules: the 84 bp sequenced amplicon 1 starts with the bases AC; amplicon 2 ends with the bases TC; and amplicon 3 ends with the bases AC. Using the same perl script both reads were interrogated to find 3 variants in the DNA fragment sequenced positioned at the coordinates 5,248,232; 5,248,233; 5,248,243. Such an approach may be employed for screening for sickle cell.

In one preferred instance, the method allows the HbS allele and the wild type HbA alleles to be distinguished. In a further preferred instance, the sequencing allows the HbS, HbC and HbA alleles to be distinguished from each other. In a further preferred instance, the method allows HbS, HbC, HbE and HbA alleles to be distinguished from each other. Hence, in one instance, the amplicons will encompass the codon for the sixth amino acid of the Beta-globin chain and in others at least one of the amplicons will also encompass codons 26 and 27. The method preferably identifies the genotype of the fetus.

In a preferred embodiment, the degree of difference in the incidence of a particular allele will be from 0.5 to 7% higher than expected, for example from 1% to 4%, in some cases from 2 to 3% and may be about 2% divergent from what would be expected from just the maternal sample on its own.

The use of a plurality of amplicons may also be employed as a control, as comparing the data for each may be used to corroborate further the results for each individual amplicon. For instance, the data for a plurality of amplicons encompassing the mutation site may be compared and in a preferred instance a diagnosis of the disorder in the fetus is assigned where a plurality and preferably all such amplicons amplified confirm the result.

In a further preferred instance, the analysis may also optionally take into account differences in sequences between two DNA fragments giving slightly different PCR efficiency and so differences in the number of copies generated from each DNA fragment after PCR. If that is seen then a bias factor can then be used to correct the allele count.

For instance, a carrier sample is amplified, such as an AS sample, which by definition has a 1:1 A to S ratio, the expected number of A and S reads is 50:50. If a departure from that ratio is seen, for example if you consistently see 48% A reads and 52% S reads for a particular amplicon, then there is a 2% bias in favour of the S allele for that particular amplicon, and that allows for correction by using the 2% bias factor to correct test data.

Hence, in one instance the method employed may comprise performing an amplification on a sample with known allelic ratio to determine whether such a bias factor exists and then preferably correcting the results obtained based on the bias factor seen. In one instance, such a control may be performed for one of the amplicons employed, preferably for two, more preferably for three of the amplicons and more preferably for all of the amplicons employed.

In one case, it may be that any bias factor for a particular sample is already known and is taken into account when analysing the results obtained. In other instances, performing such a control to determine bias factor may be part of the method of the invention and in one case such control amplifications to determine bias factor may be performed in parallel on the test sample.

Figure 4:
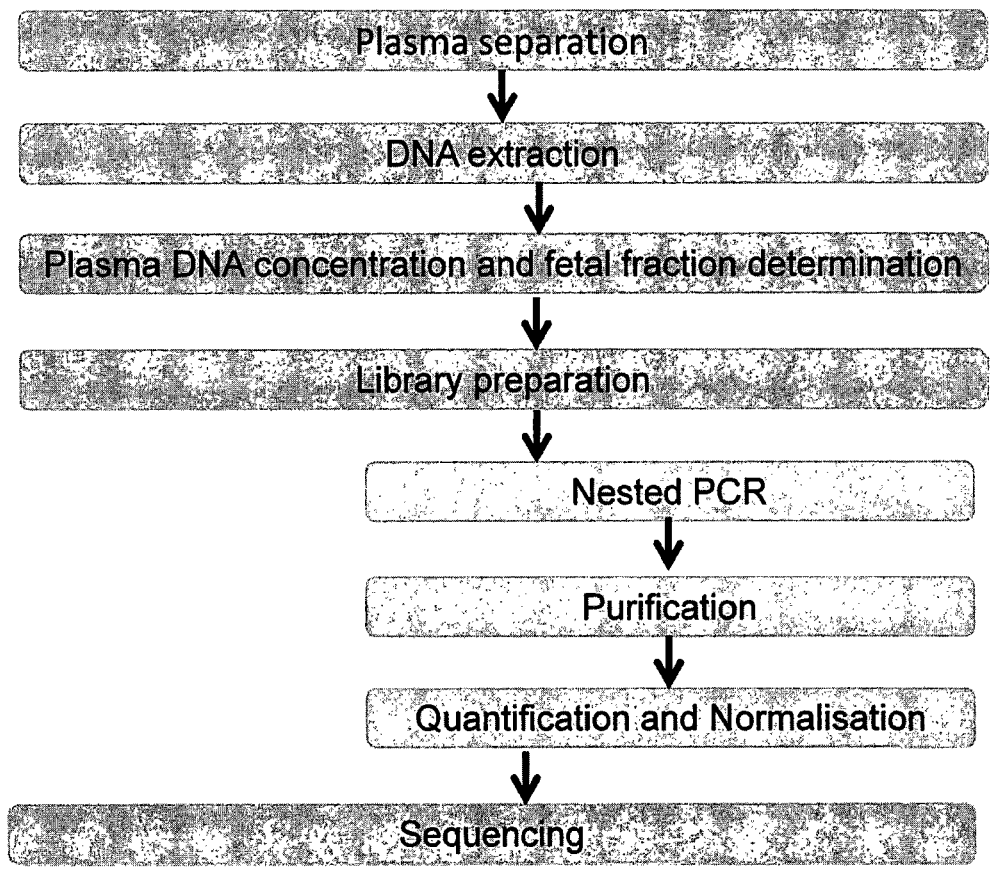
FIG. 4: Provides an illustration of one preferred embodiment of the invention in terms of sample preparation and analysis.
Figure 5:
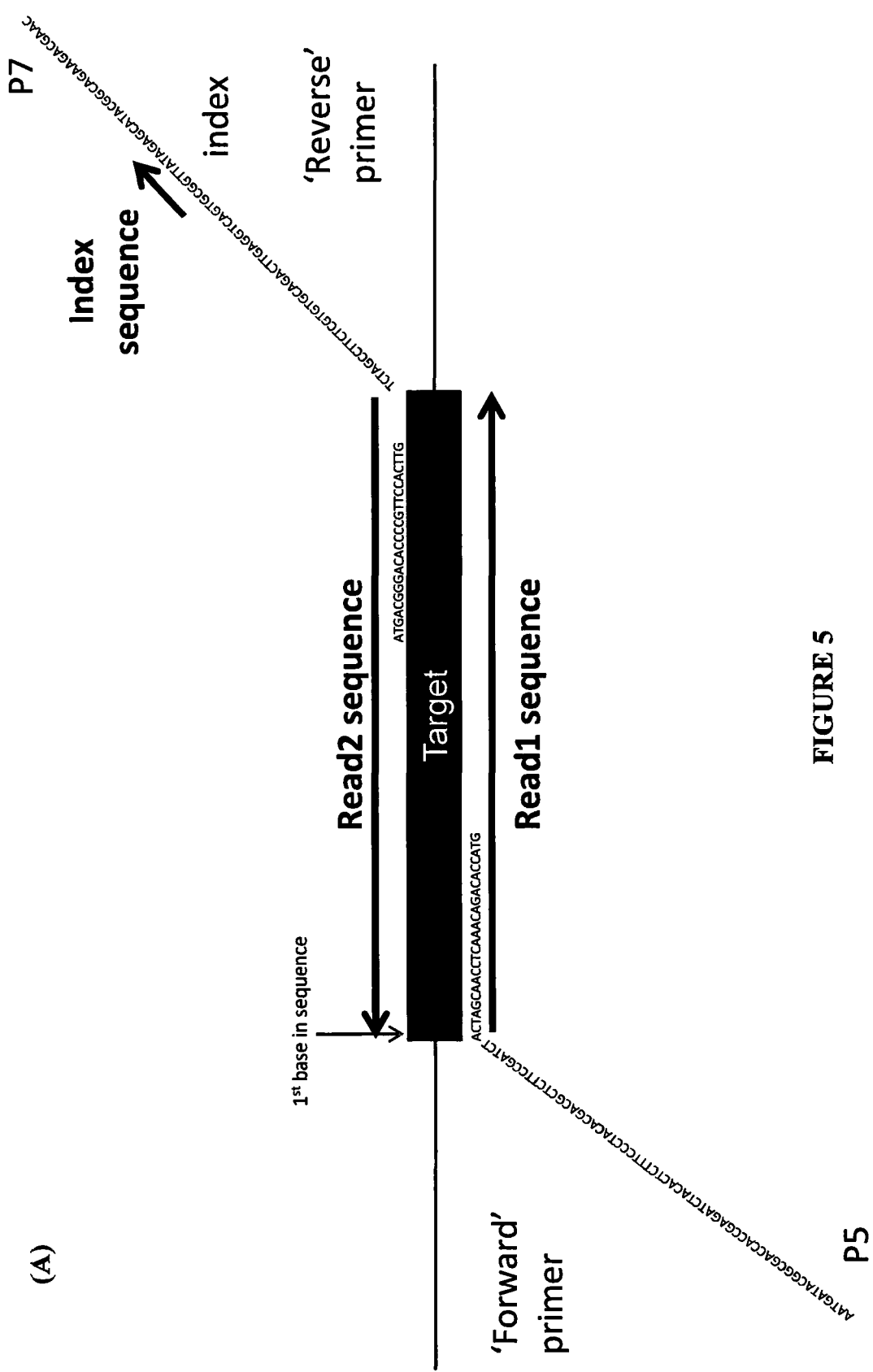
FIG. 5: Panel (A) provides a more detailed illustration of a primer pair used in the second PCR in the Examples. Panel (B) provides a summary of one possible embodiment for data analysis.

In one preferred instance, the method employed may comprise those steps indicated in FIG. 4. In a further preferred instance, the sequence analysis may comprise the steps indicated in FIG. 5.

All patents, patent applications, and other publications, including all sequences disclosed within these references, referred to herein are expressly incorporated by reference. The citation of any document is not to be construed as an admission that it is prior art with respect to the present invention.

Reference to the singular herein also encompasses the plural, unless specifically excluded. Where reference to a value is made, also disclosed is employing "about" such a value. In cases reference to "comprising" or such like is made herein, also provided are embodiments consisting of or consisting essentially of what is specified.

Examples

Methods

Sample Selection and Processing

Blood samples were obtained from women having invasive diagnostic testing for sickle cells disease. The diagnostic tests on the invasive samples were either carried out at University College Hospital Oxford or the National Haemoglobinopathy Reference Laboratory, also in Oxford. All women consented to the use of their blood or DNA in scientific research.

Whole maternal blood (between 2 and 11.5 ml) was collected into tubes containing EDTA. Plasma was separated from blood by centrifugation at 3000 rpm for 10 minutes. Then 1 ml aliquots of supernatant were transferred in 1.5 ml tubes (eppendorf) and centrifuged again at 7000 rpm for 10 minutes. Plasma was then stored in 800 µl aliquots at −80° C. until DNA extraction.

DNA Extraction

DNA was extracted from 1, 2 or 3 ml of plasma with the QIAmp Circulating Nucleic Acid kit (Qiagen). The extractions were performed according to the manufacturer's instructions using a Qiagen Vacuum manifold. The samples were eluted in 70 µl of buffer AVE.

Plasma DNA Concentration and Fetal Fraction Determination

Whenever sufficient material was available DNA concentration was assessed by real-time PCR assay to detect RASSF1A, a universal fetal DNA marker. This method allows the fetal fraction to be calculated. The method used was the same as described in White et al (2012), *Evaluation of a Novel Assay for Detection of the Fetal Marker RASSF1A: Facilitating Improved Diagnostic Reliability of Noninvasive Prenatal Diagnosis*. PLoS ONE 7(9): e45073. doi:10.1371/journal.pone.0045073. In cases where significant amounts of DNA were not available, DNA samples were quantified using the Qubit dsDNA HS assay kit (Life technologies).

Primer Selection

Six forward and six reverse primers were designed to amplify the sickle cell mutation on the HBB gene. All 36 possible combinations were evaluated for specificity and efficiency using standard molecular biology techniques (fragment sizes ranged from 66 bp to 148 bp). The best performing pairs were evaluated further using serially diluted DNA to select the three most sensitive primer sets. The primer sets are summarized below and the amplicons in FIG. 1.

Set 1: 872_HBS_F4(SEQ ID No:1)+875_HBS_R2 (SEQ ID No:2)
Set 2: 879_digSickleF (SEQ ID No:3)+875_HBS_R2 (SEQ ID No:2)
Set 3: 879_digSickleF (SEQ ID No:3)+880_disgSickleR (SEQ ID No:4)

```
                                          (SEQ ID No: 1)
872_HBS_F4 ACTAGCAACCTCAAACAGACACCATG (SEQ ID No: 2)
875_HBS_R2 GTTCACCTTGCCCCACAGGGCAGTA (SEQ ID No: 3)
879_digSickleF GCAACCTCAAACAGACACCAT (SEQ ID No: 4)
880_disgSickleR CCCCACAGGGCAGTAACG
```

Whenever there was sufficient DNA, the three primer sets were used to prepare three separate amplicons from each plasma DNA sample. The three amplicons overlap the same region of the HBB gene (see FIG. 1).

Primary Amplification and Library Preparation

Figure 2:
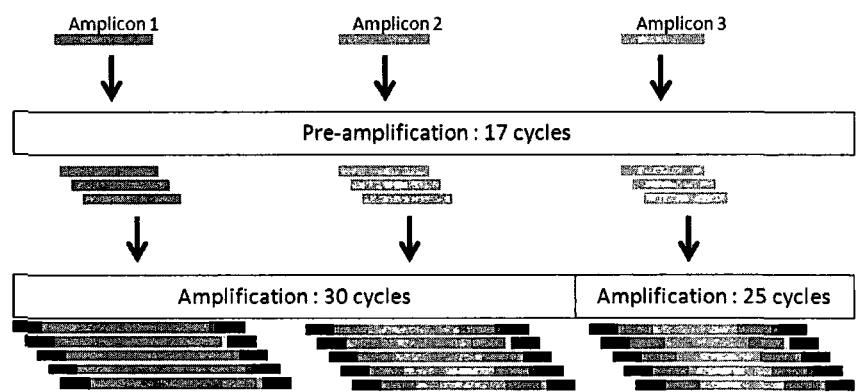
FIG. 2: Panel (A) illustrates a two step PCR, an initial preamplification is performed, followed by a second amplification to introduce additional sequences into the PCR products to help sequencing and analysis. Panel (B) shows an example of a primer for use in the second PCR and the non-template sequences it introduces into the amplification product.
Figure 2:
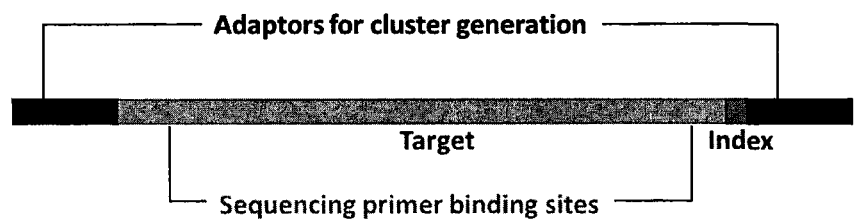

A two steps single-plex PCR amplification was performed to reduce allelic loss. During the first PCR the three sets of primers were used in a short amplification. Following this pre-amplification, a second PCR was performed to attach the appropriate adaptors, primer binding sites and barcodes essential for sequencing (see FIG. 2)

In the second PCR, Illumina specific adaptors needed for cluster generation and sequencing primer binding sites are attached at the end of both forward and reverse primers. An extra sequence is included on the reverse primer, a "barcode" generating a unique tag for each amplicon. This barcode is 6 bp long and five different barcodes were used allowing the sequencing of the same amplicon for three different patients on the same run (see FIG. 2).

Hence, the first primer pair employed was:
Forward Primer:

```
                                         (SEQ ID NO: 22)
AATGATACGGCGACCACCGAGATCTACACTCTTTCCCTACACGACGCTCT

TCCGATCT
```

Reverse Primer:

```
                                         (SEQ ID NO: 23)
CAAGCAGAAGACGGCATACGAGATGTGACTGGAGTTCAGACGTGTGCTCT

TCCGATCT
```

The index sequence was added between nucleotides 24 and 25 of the reverse primer sequence above.

```
                                          (SEQ ID NO: 5)
              Index6: ATTGGC (SEQ ID NO: 6)
              Index12: TACAAG (SEQ ID NO: 7)
              Index4: TGGTCA
```

-continued

Index5: CACTGT (SEQ ID NO: 8)

Index7: GATCTG (SEQ ID NO: 9)

Overall: the three primer pairings for the second PCR were as follows:
Amplicon 1:

F4_seq
(SEQ ID No: 10)
AATGATACGGCGACCACCGAGATCTACACTCTTTCCCTACACGACGCTCT
TCCGATCT...

R2_seq
(SEQ ID No: 11)
CAAGCAGAAGACGGCATACGAGATGTGACTGGAGTTCAGACGTGTGCTCT
TCCGATCT...

where an index sequence was added between nucleotides 24 and 25 of the reverse primer sequence.
Amplicon 2:

digSF_seq
(SEQ ID No: 12)
AATGATACGGCGACCACCGAGATCTACACTCTTTCCCTACACGACGCTCT
TCCGATCT...

R2_seq
(SEQ ID No: 13)
CAAGCAGAAGACGGCATACGAGATGTGACTGGAGTTCAGACGTGTGCTCT
TCCGATCT...

where an index sequence was added between nucleotides 24 and 25 of the reverse primer sequence.
Amplicon 3:

digSF_seq
(SEQ ID No: 14)
AATGATACGGCGACCACCGAGATCTACACTCTTTCCCTACACGACGCTCT
TCCGATCT...

digSR_seq
(SEQ ID No: 15)
CAAGCAGAAGACGGCATACGAGATGTGACTGGAGTTCAGACGTGTGCTCT
TCCGATCT...

where an index sequence was added between nucleotides 24 and 25 of the reverse primer sequence.

Depending the number of samples processed in the run these indexes were always used in the same order to allow enough diversity during the sequencing.

The primary PCR was carried out in a total volume of 100 ul and contained 10 ul of plasma DNA. Then 2.5 µl of primary PCR product was used as template in the second reaction. For both amplifications a final concentration of 240 nmol/L for each primer and 0.1 U/µl of Pwo DNA polymerase (Roche) were used with 2× QIAGEN Multiplex PCR Master Mix.

Cycling conditions were 94° C. for 3 minutes, then 17 cycles (primary PCR); 25 cycles (Amplicon 3 in secondary PCR) or 30 cycles (Amplicon 1 and 2 in secondary PCR) of 94° C. for 45 seconds, 56° C. for 45 seconds and 72° C. for 1 minute followed by 72° C. for 10 minutes. The PCR products obtained were 205 bp long for amplicon 1, 203 bp for amplicon 2 and amplicon 3 was 191 bp. Finally a 3% gel was run to check the product quality.

Clean Up and Quantification of DNA Library

After amplification each sample was purified using the MinElute PCR Purification Kit (Qiagen) using a microcentrifuge according the manufacturer's instructions and eluted in 20 µl Buffer EB (10 mM Tris-Cl, pH 8.5).

A 1 µl aliquot was used for library quantification with 2100 DNA bioanalyser kit (carried out according to manufacturer's instructions). Briefly, the samples molarity was assessed on the electropherogram using the peak specific to the amplicon (between 150 and 250 bp). Each sample was then diluted in 10 mM Tris-Cl pH8.5+0.1% Tween 20 to a stock concentration of 2 nM. The samples were then pooled together in preparation for running.

Running

Up to five samples were sequenced in one run, three amplicons each. 2 nM library stocks were prepared and equal volumes of the samples were pooled together. To help ensure a good performance and high quality data, the pooled library was mixed with PhiX control library to avoid low diversity sequencing. The preparation of the libraries and loading concentration used were the same as specified in the Miseq system user guide.

Figure 3:
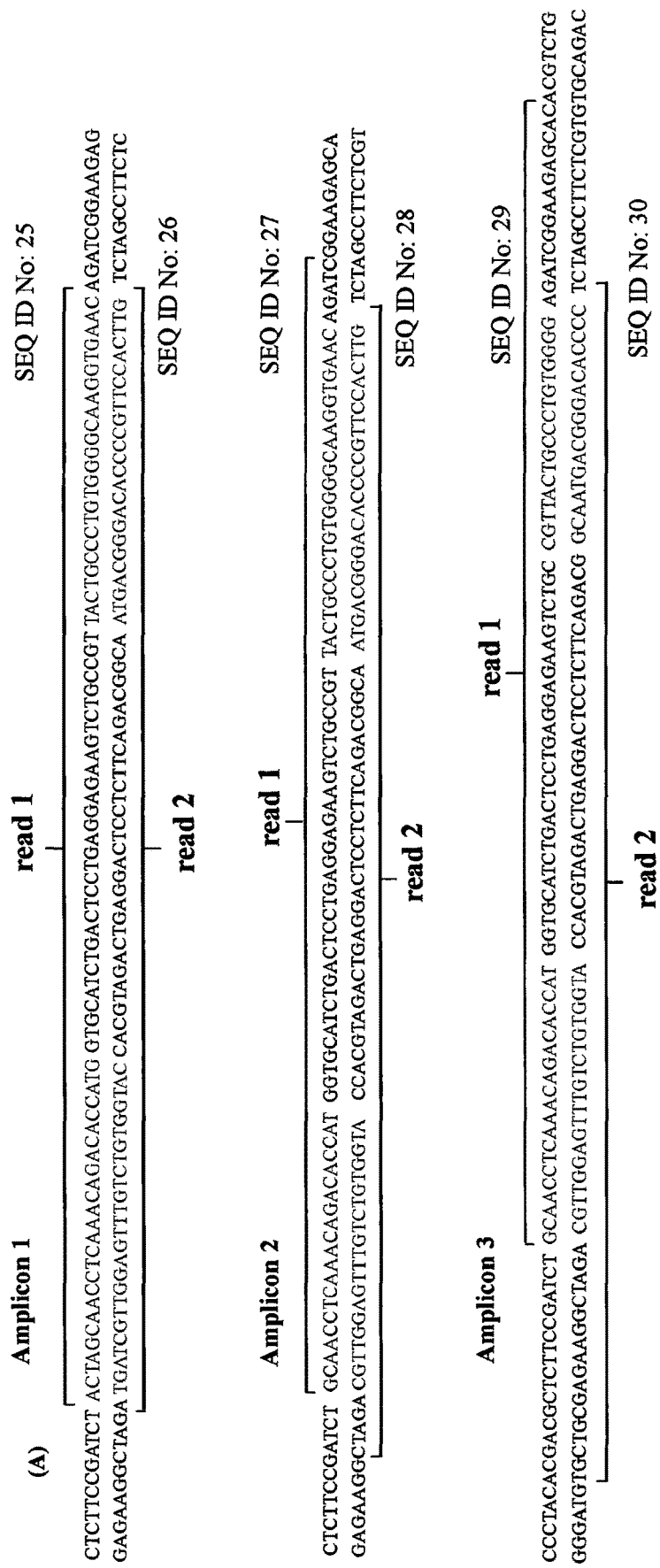
FIG. 3: Panel (A) shows the sequence of the three amplicons. Panel (B) shows the eight different alleles resulting from variation at three sites, including the site of the sickle cell anemia mutation.

A paired-end sequencing was performed using a MiSeq (illumina): 84 bases were sequenced from both ends of DNA fragments (see FIG. 3).

Data Analysis

The data was obtained in the form of FASTQ files and analysed using a Perl script.

Using the five indexes each paired-end reads were sort into samples. And using a 2 bp amplicon ID tag the reads were divided into the 3 amplicons, based on the following rules: the 84 bp sequenced amplicon 1 starts with the bases AC; amplicon 2 ends with the bases TC; and amplicon 3 ends with the bases AC.

Using the same perl script both reads were interrogated to find three variants in the DNA fragment sequenced positioned at the coordinates 5,248,232; 5,248,233; 5,248,243. Two possibilities for each variant result in 8 different sequences (see FIG. 3). The numbers of wild type and mutant variants were counted and incremented to calculate percentages.

TABLE 1

| | Sp-02 | | |
|---|---|---|---|
| Mutation | WT | MT | percent |
| AMPLICON 1 | | | |
| chr11: 5,248,232 | 585,225 | 474,912 | 44.8 |
| chr11: 5,248,233 | 1,012,182 | 47,955 | 4.5 |
| chr11: 5,248,243 | 2,143 | 1,057,994 | 99.8 |
| AMPLICON 2 | | | |
| chr11: 5,248,232 | 423,481 | 346,117 | 45.0 |
| chr11: 5,248,233 | 734,886 | 34,712 | 4.5 |
| chr11: 5,248,243 | 1,929 | 767,669 | 99.7 |
| AMPLICON 3 | | | |
| chr11: 5,248,232 | 536,131 | 458,345 | 46.1 |
| chr11: 5,248,233 | 954,365 | 40,111 | 4.0 |
| chr11: 5,248,243 | 183 | 994,293 | 100.0 |

The results illustrate that it is possible to genotype a fetus using the method of the invention.

Derivation of A/B Bias Factor

The potential differences in sequences between two DNA fragments which may, in some cases lead to slightly different PCR efficiency and noticeable differences in the number of copies generated from each DNA fragment after PCR can also be taken into account to help improve still further the results obtained. Such differences potentially result in a bias towards one or other allele (allele AB bias factor The bias factor may then be used to correct the experimental allele count to help refine the results still further.

The invention claimed is:

1. A method of diagnosing a recessive disorder or a disorder caused by a point mutation in a fetus comprising:
   (a) obtaining a cell free DNA sample from a pregnant female, wherein the sample comprises both maternal and fetal DNA;
   (b) amplifying a template region in the DNA sample encompassing a site of a mutation responsible for the disorder, wherein amplification is performed on the DNA sample by a two-step PCR process, wherein the first PCR step amplifies one or more target amplicons within a gene responsible for the disorder comprising primer pairs lacking adapter sequences and/or index sequences, wherein each primer pair amplifies a region encompassing the mutation responsible for the disorder; and
   wherein the amplification product of the first step undergoes a second PCR step, wherein the second PCR step introduces additional sequences not present in the template comprising further primer pairs, wherein each of the further primer pairs amplifies one of the target amplicons generated by the primer pairs of the first PCR step, and wherein each of the further primer pairs comprises adaptor sequences and/or index sequences not present in the template;
   (c) sequencing a plurality of amplification PCR products from the second PCR amplification step (b);
   (d) analyzing the amplification PCR products from step (c) for the frequency of incidence of the mutation in the sequenced population of the PCR products; and
   (e) diagnosing the fetus as having the disorder when divergence of the frequency of incidence of the mutation in the PCR products from step (d) as compared to the frequency expected from the maternal genotype is determined.

2. The method of claim 1, wherein
the DNA sample has been obtained from a blood sample from the pregnant female, where the blood: has been (i) spun down within about eight hours of the sample being obtained; and/or (ii) collected in a tube comprising a preservative which reduces cell free nucleic acid degradation.

3. The method of claim 1, wherein a plurality of amplicons
encompassing the mutation site are amplified.

4. The method of claim 1, where:
(a) the amplification product(s) are sequenced using next generation sequencing (NGS); and
(b) the sequencing reactions include PhiX sequences as a control.

5. The method of claim 1, where the disorder being screened for is sickle cell anemia.

6. The method of claim 1, where:
(a) the method does not comprise restriction enzyme cleavage;
(b) the method does not comprise restriction enzyme cleavage with a Type IIS restriction enzyme;
(b) the method does not comprise restriction enzyme cleavage to identify sequence variation located in the restriction enzyme cleavage site;
(c) the method does not comprise the use of filling in an overhang of a restriction enzyme cleavage site to determine sequence information;
(d) the method does not rely on the incorporation of a ddNTP to provide sequence information; and/or
(e) in the method at least two, three, four or all of (a) to (d) apply.

7. The method of claim 1, wherein the method comprises sequencing a region of at least 25, 50, 75, 100, 150 or more bases in length.

8. The method of claim 1, wherein the method:
(a) does not comprise employing a cell lysis inhibitor which comprises an aldehyde; or
(b) does comprise employing a cell lysis buffer which comprises an aldehyde.

9. The method of claim 2, where:
(a) the method comprises adding EDTA to the blood sample after collection of the blood; or
(b) the method is performed on fixed blood.

10. The method of claim 1, wherein the primer pairs in the first PCR step are selected from the group consisting of
(i) SEQ ID NO:1 and SEQ ID NO: 2;
(ii) SEQ ID NO: 3 and SEQ ID NO:2; and
(iii) SEQ ID NO:3 and SEQ ID NO:4.

11. The method of claim 1, wherein the further primer pairs in second PCR step are selected from the group consisting of:
(i) SEQ ID NO:10 and SEQ ID NO:11;
(ii) SEQ ID NO:12 and SEQ ID NO:13; and
(iii) SEQ ID NO:14 and SEQ ID NO:15.

12. The method of claim 1, wherein three amplicons encompassing the mutation site are amplified.

13. The method of claim 1, wherein the method does not comprise the use of filling in a 5' overhang of a restriction enzyme cleavage site to determine sequence information.

14. The method of claim 1, wherein the method does not entail incorporation of a ddNTP during filling in of an overhang produced by restriction enzyme digestion to provide sequence information.

15. The method of claim 1, wherein the method:
(a) does not comprise employing a cell lysis inhibitor which comprises glutaraldehyde, a derivative of glutaraldehyde, formaldehyde, a derivative of formaldehyde; or
(b) does comprise employing cell lysis inhibitor which comprises glutaraldehyde, a derivative of glutaraldehyde, formaldehyde, a derivative of formaldehyde.

16. The method of claim 1, further comprising determining an amplification bias factor for the PCR amplification product of step (b) and applying the bias factor to correct for the allelic bias in the sample to determine the correct allele count.

17. The method of claim 16, wherein the bias factor is determined by amplifying amplicons in a control sample having a known allelic ratio.

18. The method of claim 16, wherein the bias factor is determined by amplifying a plurality of amplicons in the DNA sample from the pregnant female and comparing the data from the plurality of amplicons to determine a final allelic ratio.

* * * * *

```
                            SEQUENCE LISTING

<160> NUMBER OF SEQ ID NOS: 41

<210> SEQ ID NO 1
<211> LENGTH: 26
<212> TYPE: DNA
<213> ORGANISM: Artificial Sequence
<220> FEATURE:
<223> OTHER INFORMATION: 872_HBS_F4 primer

<400> SEQUENCE: 1
actagcaacc tcaaacagac accatg                                            26

<210> SEQ ID NO 2
<211> LENGTH: 25
<212> TYPE: DNA
<213> ORGANISM: Artificial Sequence
<220> FEATURE:
<223> OTHER INFORMATION: 875_HBS_R2 primer

<400> SEQUENCE: 2
gttcaccttg ccccacaggg cagta                                             25

<210> SEQ ID NO 3
<211> LENGTH: 21
<212> TYPE: DNA
<213> ORGANISM: Artificial Sequence
<220> FEATURE:
<223> OTHER INFORMATION: 879_digSickleF primer

<400> SEQUENCE: 3
gcaacctcaa acagacacca t                                                 21

<210> SEQ ID NO 4
<211> LENGTH: 18
<212> TYPE: DNA
<213> ORGANISM: Artificial Sequence
<220> FEATURE:
<223> OTHER INFORMATION: 80_disgSickleR primer

<400> SEQUENCE: 4
ccccacaggg cagtaacg                                                     18

<210> SEQ ID NO 5
<211> LENGTH: 6
<212> TYPE: DNA
<213> ORGANISM: Artificial Sequence
<220> FEATURE:
<223> OTHER INFORMATION: Index sequence 6

<400> SEQUENCE: 5 attggc                                                                   6

<210> SEQ ID NO 6
<211> LENGTH: 6
<212> TYPE: DNA
<213> ORGANISM: Artificial Sequence
<220> FEATURE:
<223> OTHER INFORMATION: Index sequence 12

<400> SEQUENCE: 6
```

```
tacaag                                                                   6

<210> SEQ ID NO 7
<211> LENGTH: 6
<212> TYPE: DNA
<213> ORGANISM: Artificial Sequence
<220> FEATURE:
<223> OTHER INFORMATION: Index sequence 4

<400> SEQUENCE: 7 tggtca                                                                   6

<210> SEQ ID NO 8
<211> LENGTH: 6
<212> TYPE: DNA
<213> ORGANISM: Artificial Sequence
<220> FEATURE:
<223> OTHER INFORMATION: Index sequence 5

<400> SEQUENCE: 8 cactgt                                                                   6

<210> SEQ ID NO 9
<211> LENGTH: 6
<212> TYPE: DNA
<213> ORGANISM: Artificial Sequence
<220> FEATURE:
<223> OTHER INFORMATION: Index sequence 7

<400> SEQUENCE: 9 gatctg                                                                   6

<210> SEQ ID NO 10
<211> LENGTH: 84
<212> TYPE: DNA
<213> ORGANISM: Artificial Sequence
<220> FEATURE:
<223> OTHER INFORMATION: F4_seq primer

<400> SEQUENCE: 10
aatgatacgg cgaccaccga gatctacact ctttccctac acgacgctct tccgatctac        60
tagcaacctc aaacagacac catg                                              84

<210> SEQ ID NO 11
<211> LENGTH: 83
<212> TYPE: DNA
<213> ORGANISM: Artificial Sequence
<220> FEATURE:
<223> OTHER INFORMATION: R2_seq primer

<400> SEQUENCE: 11
caagcagaag acggcatacg agatgtgact ggagttcaga cgtgtgctct tccgatctgt        60
tcaccttgcc ccacagggca gta                                               83

<210> SEQ ID NO 12
<211> LENGTH: 79
<212> TYPE: DNA
<213> ORGANISM: Artificial Sequence
<220> FEATURE:
<223> OTHER INFORMATION: digSF_seq primer

<400> SEQUENCE: 12
aatgatacgg cgaccaccga gatctacact ctttccctac acgacgctct tccgatctgc        60
```
aacctcaaac agacaccat                                              79

<210> SEQ ID NO 13
<211> LENGTH: 83
<212> TYPE: DNA
<213> ORGANISM: Artificial Sequence
<220> FEATURE:
<223> OTHER INFORMATION: R2_seq primer

<400> SEQUENCE: 13
caagcagaag acggcatacg agatgtgact ggagttcaga cgtgtgctct tccgatctgt    60
tcaccttgcc ccacagggca gta                                           83

<210> SEQ ID NO 14
<211> LENGTH: 79
<212> TYPE: DNA
<213> ORGANISM: Artificial Sequence
<220> FEATURE:
<223> OTHER INFORMATION: digSF_seq primer

<400> SEQUENCE: 14
aatgatacgg cgaccaccga gatctacact ctttccctac acgacgctct tccgatctgc    60
aacctcaaac agacaccat                                                79

<210> SEQ ID NO 15
<211> LENGTH: 76
<212> TYPE: DNA
<213> ORGANISM: Artificial Sequence
<220> FEATURE:
<223> OTHER INFORMATION: digSR_seq primer

<400> SEQUENCE: 15
caagcagaag acggcatacg agatgtgact ggagttcaga cgtgtgctct tccgatctcc    60
ccacagggca gtaacg                                                   76

<210> SEQ ID NO 16
<211> LENGTH: 24
<212> TYPE: DNA
<213> ORGANISM: Artificial Sequence
<220> FEATURE:
<223> OTHER INFORMATION: Part of R2_seq primer

<400> SEQUENCE: 16
caagcagaag acggcatacg agat                                          24

<210> SEQ ID NO 17
<211> LENGTH: 59
<212> TYPE: DNA
<213> ORGANISM: Artificial Sequence
<220> FEATURE:
<223> OTHER INFORMATION: Part of R2_seq primer

<400> SEQUENCE: 17
gtgactggag ttcagacgtg tgctcttccg atctgttcac cttgccccac agggcagta    59

<210> SEQ ID NO 18
<211> LENGTH: 24
<212> TYPE: DNA
<213> ORGANISM: Artificial Sequence
<220> FEATURE:
<223> OTHER INFORMATION: Part of R2_seq primer

<400> SEQUENCE: 18
caagcagaag acggcatacg agat                                          24

<210> SEQ ID NO 19
<211> LENGTH: 59
<212> TYPE: DNA
<213> ORGANISM: Artificial Sequence
<220> FEATURE:
<223> OTHER INFORMATION: Part of R2_seq primer

<400> SEQUENCE: 19
gtgactggag ttcagacgtg tgctcttccg atctgttcac cttgccccac agggcagta          59

<210> SEQ ID NO 20
<211> LENGTH: 24
<212> TYPE: DNA
<213> ORGANISM: Artificial Sequence
<220> FEATURE:
<223> OTHER INFORMATION: Part of digSR_seq primer

<400> SEQUENCE: 20
caagcagaag acggcatacg agat                                                24

<210> SEQ ID NO 21
<211> LENGTH: 52
<212> TYPE: DNA
<213> ORGANISM: Artificial Sequence
<220> FEATURE:
<223> OTHER INFORMATION: Part of digSR_seq primer

<400> SEQUENCE: 21
gtgactggag ttcagacgtg tgctcttccg atctccccac agggcagtaa cg                 52

<210> SEQ ID NO 22
<211> LENGTH: 58
<212> TYPE: DNA
<213> ORGANISM: Artificial Sequence
<220> FEATURE:
<223> OTHER INFORMATION: Forward primer cited in Examples

<400> SEQUENCE: 22
aatgatacgg cgaccaccga gatctacact ctttccctac acgacgctct tccgatct           58

<210> SEQ ID NO 23
<211> LENGTH: 58
<212> TYPE: DNA
<213> ORGANISM: Artificial Sequence
<220> FEATURE:
<223> OTHER INFORMATION: Reverse primer cited in Examples

<400> SEQUENCE: 23
caagcagaag acggcatacg agatgtgact ggagttcaga cgtgtgctct tccgatct           58

<210> SEQ ID NO 24
<211> LENGTH: 91
<212> TYPE: DNA
<213> ORGANISM: Homo Sapiens

<400> SEQUENCE: 24
gttcactagc aacctcaaac agacaccatg gtgcatctga ctcctgagga gaagtctgcc          60
gttactgccc tgtggggcaa ggtgaacgtg g                                        91

<210> SEQ ID NO 25
<211> LENGTH: 107
<212> TYPE: DNA
<213> ORGANISM: Artificial Sequence
<220> FEATURE:

<223> OTHER INFORMATION: Amplicon 1

<400> SEQUENCE: 25

```
ctcttccgat ctactagcaa cctcaaacag acaccatggt gcatctgact cctgaggaga    60
agtctgccgt tactgccctg tggggcaagg tgaacagatc ggaagag                 107
```

<210> SEQ ID NO 26
<211> LENGTH: 107
<212> TYPE: DNA
<213> ORGANISM: Artificial Sequence
<220> FEATURE:
<223> OTHER INFORMATION: Amplicon 1 (complementary)

<400> SEQUENCE: 26

```
ctcttccgat ctgttcacct tgccccacag ggcagtaacg gcagacttct cctcaggagt    60
cagatgcacc atggtgtctg tttgaggttg ctagtagatc ggaagag                 107
```

<210> SEQ ID NO 27
<211> LENGTH: 105
<212> TYPE: DNA
<213> ORGANISM: Artificial Sequence
<220> FEATURE:
<223> OTHER INFORMATION: Amplicon 2

<400> SEQUENCE: 27

```
ctcttccgat ctgcaacctc aaacagacac catggtgcat ctgactcctg aggagaagtc    60
tgccgttact gccctgtggg gcaaggtgaa cagatcggaa gagca                   105
```

<210> SEQ ID NO 28
<211> LENGTH: 105
<212> TYPE: DNA
<213> ORGANISM: Artificial Sequence
<220> FEATURE:
<223> OTHER INFORMATION: Amplicon 2 (complementary)

<400> SEQUENCE: 28

```
tgctcttccg atctgttcac cttgccccac agggcagtaa cggcagactt ctcctcagga    60
gtcagatgca ccatggtgtc tgtttgaggt tgcagatcgg aagag                   105
```

<210> SEQ ID NO 29
<211> LENGTH: 115
<212> TYPE: DNA
<213> ORGANISM: Artificial Sequence
<220> FEATURE:
<223> OTHER INFORMATION: Amplicon 3

<400> SEQUENCE: 29

```
ccctacacga cgctcttccg atctgcaacc tcaaacagac accatggtgc atctgactcc    60
tgaggagaag tctgccgtta ctgccctgtg gggagatcgg aagagcacac gtctg        115
```

<210> SEQ ID NO 30
<211> LENGTH: 115
<212> TYPE: DNA
<213> ORGANISM: Artificial Sequence
<220> FEATURE:
<223> OTHER INFORMATION: Amplicon 3 (complementary)

<400> SEQUENCE: 30

```
cagacgtgtg ctcttccgat ctccccacag ggcagtaacg gcagacttct cctcaggagt    60
cagatgcacc atggtgtctg tttgaggttg cagatcggaa gagcgtcgtg taggg        115
```

```
<210> SEQ ID NO 31
<211> LENGTH: 84
<212> TYPE: DNA
<213> ORGANISM: Homo Sapiens

<400> SEQUENCE: 31
actagcaacc tcaaacagac accatggtgc atctgactcc tgaggagaag tctgccgtta    60
ctgccctgtg gggcaaggtg aaca                                           84

<210> SEQ ID NO 32
<211> LENGTH: 30
<212> TYPE: DNA
<213> ORGANISM: Artificial Sequence
<220> FEATURE:
<223> OTHER INFORMATION: Allele resulting from variation at 3 sites

<400> SEQUENCE: 32
ggtgcatctg actcctgagg agaagtctgc                                     30

<210> SEQ ID NO 33
<211> LENGTH: 30
<212> TYPE: DNA
<213> ORGANISM: Artificial Sequence
<220> FEATURE:
<223> OTHER INFORMATION: Allele resulting from variation at 3 sites

<400> SEQUENCE: 33
ggtgcacctg actcctgagg agaagtctgc                                     30

<210> SEQ ID NO 34
<211> LENGTH: 30
<212> TYPE: DNA
<213> ORGANISM: Artificial Sequence
<220> FEATURE:
<223> OTHER INFORMATION: Allele resulting from variation at 3 sites

<400> SEQUENCE: 34
ggtgcatctg actcctaagg agaagtctgc                                     30

<210> SEQ ID NO 35
<211> LENGTH: 30
<212> TYPE: DNA
<213> ORGANISM: Artificial Sequence
<220> FEATURE:
<223> OTHER INFORMATION: Allele resulting from variation at 3 sites

<400> SEQUENCE: 35
ggtgcacctg actcctaagg agaagtctgc                                     30

<210> SEQ ID NO 36
<211> LENGTH: 30
<212> TYPE: DNA
<213> ORGANISM: Artificial Sequence
<220> FEATURE:
<223> OTHER INFORMATION: Allele resulting from variation at 3 sites

<400> SEQUENCE: 36
ggtgcatctg actcctgtgg agaagtctgc                                     30

<210> SEQ ID NO 37
<211> LENGTH: 30
<212> TYPE: DNA
<213> ORGANISM: Artificial Sequence
<220> FEATURE:
<223> OTHER INFORMATION: Allele resulting from variation at 3 sites
```

```
<400> SEQUENCE: 37
ggtgcacctg actcctgtgg agaagtctgc                                        30

<210> SEQ ID NO 38
<211> LENGTH: 30
<212> TYPE: DNA
<213> ORGANISM: Artificial Sequence
<220> FEATURE:
<223> OTHER INFORMATION: Allele resulting from variation at 3 sites

<400> SEQUENCE: 38
ggtgcatctg actcctatgg agaagtctgc                                        30

<210> SEQ ID NO 39
<211> LENGTH: 30
<212> TYPE: DNA
<213> ORGANISM: Artificial Sequence
<220> FEATURE:
<223> OTHER INFORMATION: Allele resulting from variation at 3 sites

<400> SEQUENCE: 39
ggtgcacctg actcctatgg agaagtctgc                                        30

<210> SEQ ID NO 40
<211> LENGTH: 84
<212> TYPE: DNA
<213> ORGANISM: Artificial Sequence
<220> FEATURE:
<223> OTHER INFORMATION: Amplicon 2, figure 6

<400> SEQUENCE: 40
gcaacctcaa acagacacca tggtgcatct gactcctgag gagaagtctg ccgttactgc       60
cctgtggggc aaggtgaaca gatc                                              84

<210> SEQ ID NO 41
<211> LENGTH: 84
<212> TYPE: DNA
<213> ORGANISM: Artificial Sequence
<220> FEATURE:
<223> OTHER INFORMATION: Amplicon 3, figure 6

<400> SEQUENCE: 41
gcaacctcaa acagacacca tggtgcatct gactcctgag gagaagtctg ccgttactgc       60
cctgtgggga gatcggaaga gcac                                              84
```